United States Patent
Jiang et al.

(10) Patent No.: US 7,292,985 B2
(45) Date of Patent: Nov. 6, 2007

(54) DEVICE AND METHOD FOR REDUCING STUTTERING

(75) Inventors: Tao Jiang, Chengdu (CN); Xiaoyi Fu, Chengdu (CN); Yining Jiang, Chengdu (CN); Shixiong Xia, Chengdu (CN); Alan Newton, Greenville, NC (US)

(73) Assignee: Janus Development Group, Greenville, NC (US)

( * ) Notice: Subject to any disclaimer, the term of this patent is extended or adjusted under 35 U.S.C. 154(b) by 140 days.

(21) Appl. No.: 11/001,722

(22) Filed: Dec. 2, 2004

(65) Prior Publication Data

US 2006/0122826 A1    Jun. 8, 2006

(51) Int. Cl.
*G10L 21/00* (2006.01)
(52) U.S. Cl. .................. 704/271; 381/312
(58) Field of Classification Search .............. None
See application file for complete search history.

(56) References Cited

U.S. PATENT DOCUMENTS

| | | | | |
|---|---|---|---|---|
| 5,133,013 | A * | 7/1992 | Munday | 704/226 |
| 5,500,902 | A | 3/1996 | Stockham, Jr. et al. | |
| 5,550,924 | A * | 8/1996 | Helf et al. | 381/94.3 |
| 5,602,962 | A * | 2/1997 | Kellermann | 704/226 |
| 5,647,834 | A | 7/1997 | Ron | |
| 5,794,203 | A | 8/1998 | Kehoe | |
| 5,848,171 | A | 12/1998 | Stockham, Jr. et al. | |
| 5,937,377 | A * | 8/1999 | Hardiman et al. | 704/225 |
| 5,940,798 | A | 8/1999 | Houde | |
| 5,961,443 | A | 10/1999 | Rastatter et al. | |
| 6,044,162 | A | 3/2000 | Mead et al. | |
| 6,072,885 | A | 6/2000 | Stockham, Jr. et al. | |
| 6,233,549 | B1 * | 5/2001 | Mauro et al. | 704/207 |
| 6,356,067 | B1 * | 3/2002 | Nara | 324/76.23 |
| 6,754,632 | B1 | 6/2004 | Kalinowski et al. | |

\* cited by examiner

*Primary Examiner*—Abul K. Azad
(74) *Attorney, Agent, or Firm*—MacCord Mason PLLC

(57) ABSTRACT

The present invention is directed to a wearable stutter reducing device incorporating novel methods that make extensive use of digital signal processing (DSP) technology. The wearable stutter reducing device of the present invention has an audio signal receiver for receiving speech signals corresponding to a wearer's voice. An input conversion means for converting the speech signals and noise mixed with the speech signals into frequency domain components is in communication with the audio signal receiver. A channelization means in communication with the conversion means separates the frequency domain components into a plurality of channels. An identifying means in communication with the plurality of channels identifies which channels of the plurality of channels contain substantially more speech corresponding frequency domain components than noise corresponding frequency components. An amplification means for amplifying signals identified as speech is in communication with the identifying means. The present invention also includes a frequency altering means for altering the frequency of a predetermined number of channels and an output conversion means in communication with the amplification means for converting the frequency components into time domain signals containing amplified speech.

22 Claims, 9 Drawing Sheets

DEVICE AND METHOD FOR REDUCING STUTTERING

BACKGROUND OF THE INVENTION

1. Field of the Invention

The present invention relates to a device and method for reducing stuttering. In particular, the present invention relates to electronic devices and methods employing altered audio feedback to minimize stuttering.

2. Description of the Prior Art

Background noise continues to be an annoying problem for people wearing hearing devices that incorporate altered audio feedback to minimize stuttering. Typically, people who benefit from altered audio feedback have normal hearing sensitivity. As a result, this special population suffers background noise annoyance to a greater extent than people that use hearing aids as a treatment for hearing loss.

Presently, there are some anti-stuttering devices that reduce background noise. For example, Casa Futura Technologies of 720 31$^{st}$ Street, Boulder Colo., makes use of various methods to minimize the impact of background noise. Their primary approach appears to be the use of noise canceling directional microphones that pick up a user's voice while somewhat rejecting background noise. Casa Futura also incorporates high-frequency filters to attenuate background noise above the user's normal vocal range. They also use hearing aid like expansion techniques to amplify the user's voice while making the background quieter. Moreover, Casa Futura uses a voice activated switch to turn on voice amplification when the user speaks and off when the user stops speaking.

Beyond background noise reduction, most manufactures of anti-stuttering technology also employ frequency-altered feedback (FAF) to enhance the fluency of people who stutter. Presently, most manufacturers shift the entire frequency range of audibility in order to produce FAF effects on the user. The frequency of audibility used by most manufacturers is between 20 to 6000 Hz. Some others use a reduced range from between 60 to 3500 Hz. In either case, the entire frequency range is shifted either up or down to be used as feedback to the user. However, shifting the entire audibility frequency range tends to mangle the fundamental frequency of speech, thus producing noticeable voice distortion to the user. As a result, voice distortion is a main complaint among users.

While all the above approaches are somewhat effective, they tend to be less than ideal. What is needed is a frequency-altered feedback technology that significantly reduces noticeable voice distortion within the components of speech used as feedback to the user. Moreover, there is a need for an anti-stuttering device having unique noise attenuation functions that can significantly increase how long a stuttering patient can tolerate wearing his or her anti-stuttering device.

SUMMARY OF THE INVENTION

The present invention is a wearable stutter reducing device that addresses this need by incorporating novel methods that make extensive use of digital signal processing (DSP) technology. The wearable stutter reducing device of the present invention has an audio signal receiver for receiving speech signals corresponding to a wearer's voice. Preferably the audio signal receiver comprises an input audio transducer in communication with an analog-to-digital converter circuit. An input conversion means for converting the speech signals and noise mixed with the speech signals into frequency domain components is in communication with the audio signal receiver. The preferred input conversion means is a digital signal processor programmed with a fast Fourier transform algorithm. A channelization means in communication with the conversion means separates the frequency domain components into a plurality of channels. The preferred channelization means is a plurality of digital filters. Preferably, the digital filters are implemented through software or firmware executable by the digital signal processor.

An identifying means in communication with the plurality of channels identifies which channels of the plurality of channels contain substantially more speech corresponding frequency domain components than noise corresponding frequency components. The preferred identifying means is a digital signal processor having software that searches through the plurality of channels to identify channels containing predominately speech signals or predominately noise. An amplification means relatively amplifies signals identified as speech is in communication with the identifying means. In particular, the amplification means is adjustable to exclusively amplify channels identified as containing substantially more speech corresponding components than noise corresponding components. The preferred amplification means is a digital signal processor having software that is executable to increase the amplitude of speech corresponding components. An output conversion means in communication with the amplification means converts the frequency components into discrete time domain signals containing amplified speech. The preferred output conversion means is a digital signal processor including software or firmware to implement an inverse fast Fourier transform. A digital-to-analog converter receives the discrete time domain signals and converts then to analog signals for output to an output audio transducer, such as an audio frequency speaker.

The methods of the present invention employ sophisticated digital signal processing to analyze audio input signals and classify them into various groups. In a first method, the audio input signals are analyzed in both the time and frequency domains so that the user's voice is accurately identified and effectively maintained while other undesirable signals such as background noise are reduced. In particular, the present invention intelligently screens incoming audio signals and classifies them as desirable or undesirable. After classification, the received undesirable audio signals are effectively reduced either by their own attenuation or by the amplification of the desirable audio signals or by a combination of both noise attenuation and desirable signal amplification. The steps comprising this first method for reducing stuttering using a wearable stutter reducing device include:

a) receiving audio signals corresponding to the person's speech mixed with noise;

b) converting said audio signals into frequency domain components;

c) channelizing said frequency domain components into a plurality of channels;

d) identifying which of said plurality of channels contain substantially more speech corresponding frequency domain components than noise corresponding frequency domain components;

e) increasing the amplitudes of frequency domain components within the channels identified as containing substantially more speech corresponding components than noise corresponding components relative to the amplitudes of frequency domain components within channels containing substantially more noise than speech components; and f) converting said channelized frequency domain components into an audible time domain signal.

In a second method, select frequency bands of the audio input signals are altered in frequency and are used as feedback to the user by way of reconstructed sound. For the purposes of this disclosure, this second method will be referred to as band based frequency altered feedback or b-FAF. In contrast to traditional frequency altered feedback, b-FAF frequency shifts only a few select bands of the audio input signals, whereas traditional frequency altered feedback techniques frequency shifts all audible bands of the received audio signals.

In a preferred embodiment, the speech or voice spectrum is broken down into 500 Hz bands or smaller. Only one or two of these 500 Hz or smaller bands are then shifted in frequency. Moreover, it is preferred that only bands within a certain range are shifted. For example, two bands below a 1000 Hz may be selected as the bands to shift, leaving all the bands above 1000 Hz at their natural frequency. In this way, there is much less impact on the reconstructed speech that is used as feedback. In other words, from the point of speech perception, b-FAF does not alter the frequencies making up speech information that is unique to the user. Therefore, b-FAF offers much less distortion while at the same time preserves all the good attributes of traditional FAF. The steps comprising this second method include:

a) receiving an audio signal corresponding to the person's speech;

b) converting said audio signal into frequency domain components;

c) channelizing said frequency domain components into a first predetermined number of channels;

d) altering the frequency of a second predetermined number of said first predetermined number of channels, wherein said second predetermined number of channels is less than said first predetermined of channels; and e) converting said channelized frequency domain components of said first predetermined number of channels into an audible time domain signal.

In operation, the wearable stutter reducing device of the present invention is placed in communication with at least one of the user's ears. The device is powered and the input audio transducer receives a mixed signal made up of the user's speech along with any ambient and internal noise. The digital-to-analog converter converts the mixed signal into a digital signal stream that is analyzed by the digital signal processor. The digital signal processor uses the fast Fourier transform firmware to channelize the digital stream into the predetermined number of channels. One or more characters of the mixed signal are extracted and used by the digital signal processor to determine which channels predominately contain speech and which channels predominately contain noise. The channels predominately containing speech components are amplified relative to channels predominately containing noise. The relative amplification of the channels predominately containing speech is accomplished by relatively increasing the amplitude of components within those channels while leaving the channels containing noise at their original amplitudes or by attenuating the channels containing noise while leaving the channels dominated by speech components at their original amplitudes or by amplifying channels dominated by speech components while also attenuating channels dominated by noise. The digital signal processor also alters the frequency of the second predetermined number of channels. This processed digital data stream is then turned into a time domain signal using the inverse fast Fourier transform programmed into the digital signal processor. The resulting signal is then converted from its digital form into an analog signal for output to the speaker through the analog-to-digital converter. These and other aspects of the present invention will become apparent to those skilled in the art after a reading of the following description of the preferred embodiment.

DETAILED DESCRIPTION OF THE INVENTION

The preferred embodiment of the present invention is based upon multi-channel processing that enhances speech signals by suppressing undesirable background noise by utilizing a spectrum subtraction principle. The purpose of suppressing undesirable background noise is to increase the intelligibility of speech in noise.

Figure 1:
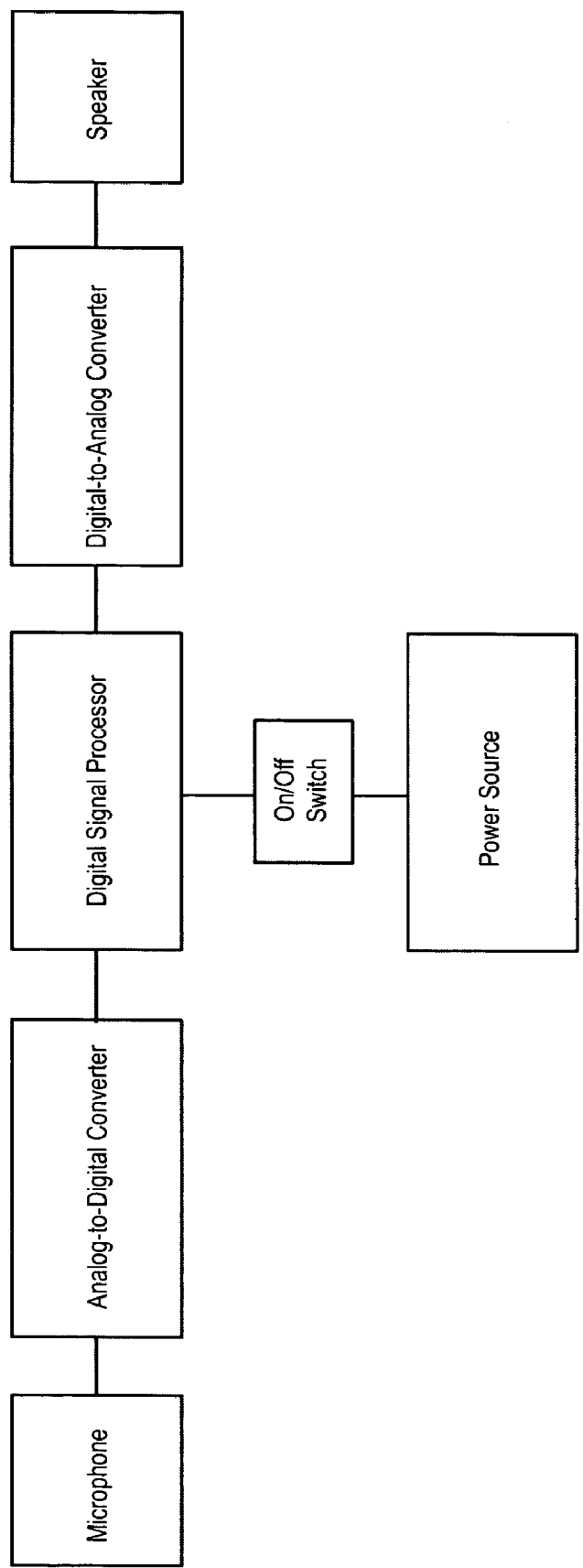
FIG. 1 is a block diagram of the wearable stutter reducing device of the present invention.

FIG. 1 is a block diagram of the wearable stutter reducing device of the present invention. As shown in FIG. 1, the device of the present invention generally comprises a microphone useable as an input audio transducer. An analog-digital converter in communication with the microphone converts analog audio signals received by the microphone into a digital audio stream. A digital signal processor (DSP) in communication with the analog-to-digital converter receives the digital audio stream and processes it in accordance with the methods of the present invention. A digital-to-analog converter in communication with the digital signal processor converts a processed digital audio stream into analog signals for output. A speaker in communication with the digital-to-analog converter transmits sound waves corresponding to the digital-to-analog converter's output analog signals. A power source such as an electrochemical battery powers the device. An electrical on/off switch is useable to turn off the device when not in use to conserve battery life. Not shown are optional features such as analog low-pass filters that can be added between the microphone and the analog-to-digital converter and in between the digital-to-analog converter and the speaker. Moreover, the device of the present invention is preferably housed in a behind-the-ear or in-the-ear canal housing such as either of those shown in FIGS. 5A and 5B of U.S. Pat. No. 6,754,632 to Kalinowski et al., the contents of which are hereby incorporated by reference as if recited in full herein.

Figure 2:
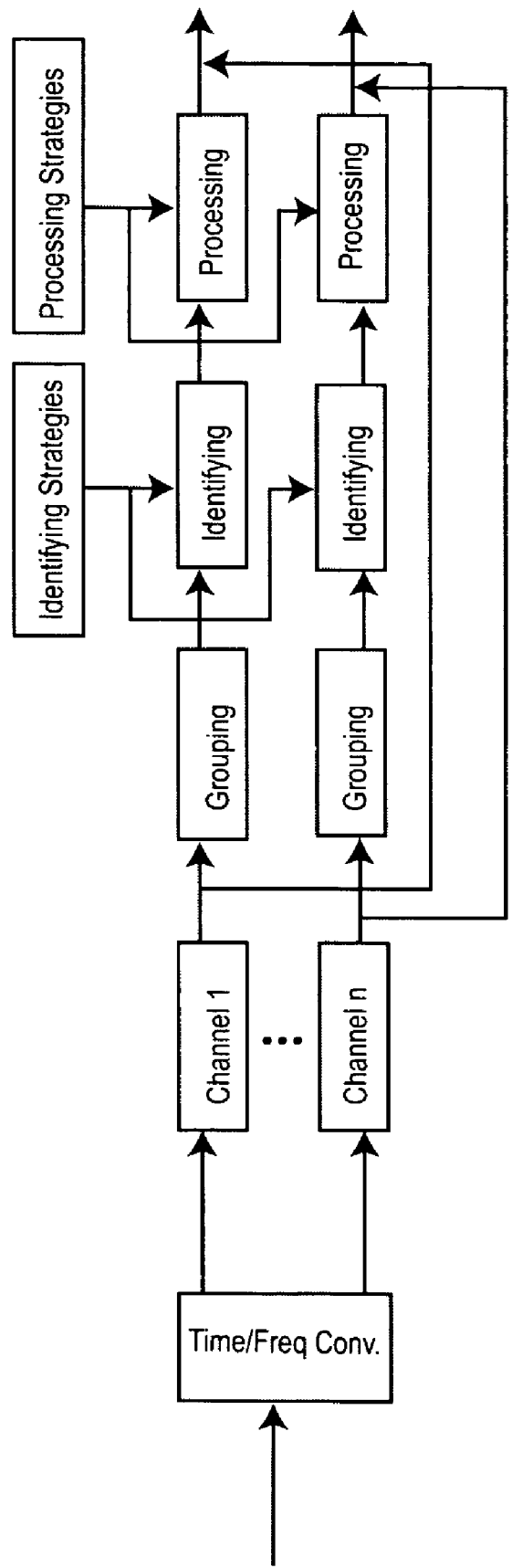
FIG. 2 is a block diagram illustrating a pathway for signals.

FIG. 2 is a block diagram illustrating a pathway for signals. First, an incoming audio signal containing a mixture of speech and noise is converted from the time domain to the frequency domain. In other words, the incoming audio signal is broken down into various frequency components for processing. These frequency components are then grouped according to a set of pre-established criteria. For example, at this stage, the frequency components of speech are identified and amplified, and the frequency components attributed to noise are maintained at their current level or preferably attenuated. Thus, the signal to noise ratio of the audio signal is increased.

Figure 3:
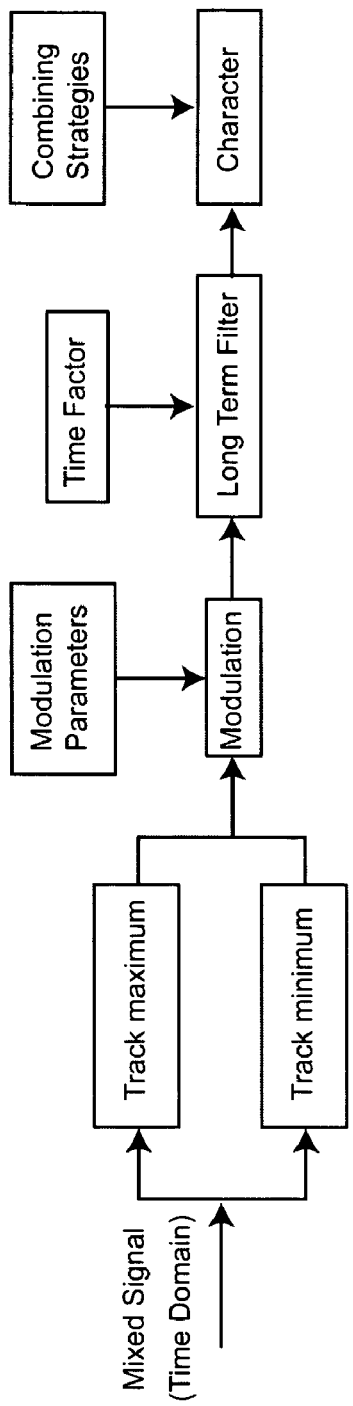
FIG. 3 is a block diagram depicting the extraction of characteristics belonging to speech signals mixed with noise.
Figure 4:
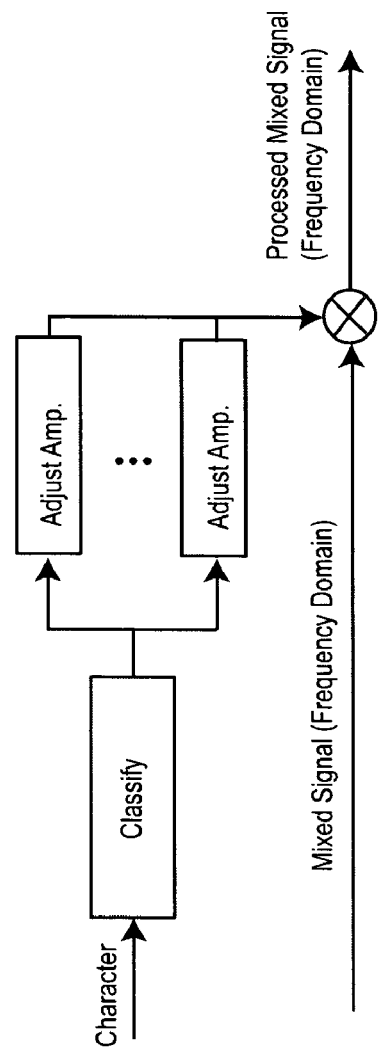
FIG. 4 is a block diagram showing classification of the characteristics used to adjust amplifiers.

In order for the above steps to be realized, at least one character of the signals must be identified. Signal intensity, intensity change ratio and or duration are all characteristics of the mixed noise and speech signals that can be exploited to group the signal's frequency components. FIGS. 3 and 4 are block diagrams depicting the extraction of characteristics belonging to speech signals mixed with noise, whereby the characteristics are used to adjust amplifiers used to amplify the frequency components of speech. In FIG. 3, a time domain mixed signal (i.e., speech mixed with noise) is tracked by maximum and minimum tracking functions that capture the minimum and maximum intensities of the signal. A modulation parameter together with a time factor and combining strategies extract a character of the signal. The signal character under goes classification as shown in FIG. 4. The results of the classification are then used to adjust a plurality of adjustable amplifiers.

Figure 5:
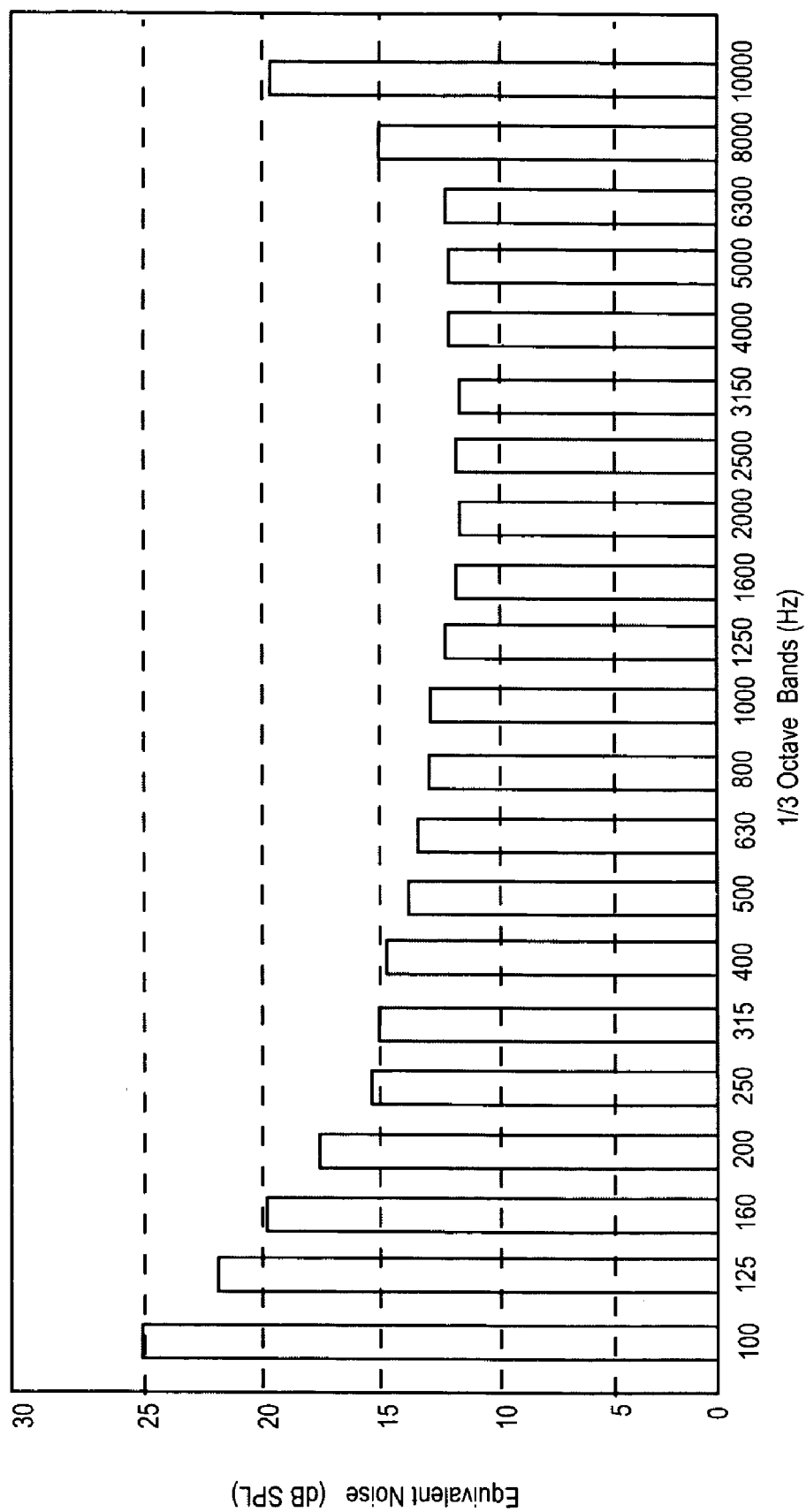
FIG. 5 is a bar graph of a wide band audio signal due to internal noise of microphone.
Figure 6:
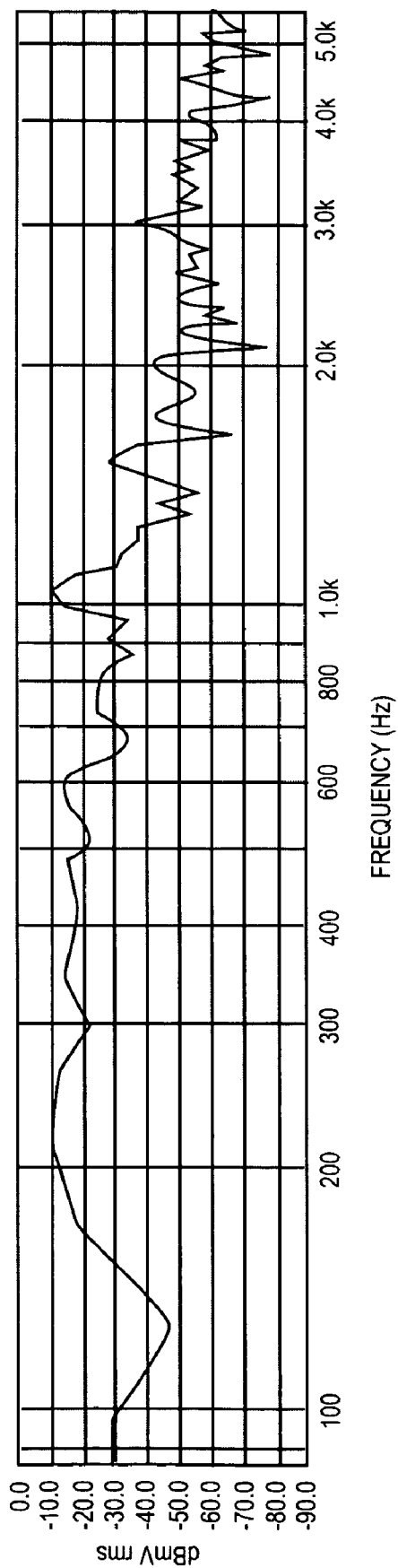
FIG. 6 is a line graph of the intensity characteristic of a typical speech signal.

FIG. 5 illustrates the wide band audio signal due to internal noise of a microphone. Noise tends to be continuous whereas speech is far less continuous. Therefore, one character of this internal noise signal is well-proportioned intensity. In contrast, as shown in FIG. 6, the intensity characteristic of speech is not well proportioned and changes rapidly. Therefore, in this case, the difference in the intensity characteristics between the speech components and the noise components of the mixed signal can be compared to set a dynamic threshold for amplification.

Strategies for extracting characteristics, identifying or processing signals are pre-established according to the various expected environments of operation. A process called "training" for the purposes of this application can be used to analyze typical inputs to determine different strategies accordingly. Training can be implemented on a typical personal computer equipped with a sound card and audio signal processing software. For example, a mixed signal made up of a 1000 Hz tone burst and white noise can be processed as follows. Every 1000 ms there is a tune burst having a maximum peak amplitude of 0 dBmv and a minimum amplitude of −10 dBmv. On the other hand, the white noise maximum amplitude never reaches 0 dBmv. Therefore, the maximum peak amplitude of 0 dBmv can be used as an identifiable characteristic of the 1000 Hz tone burst. Therefore, if a mixed signal content exceeds −10 dBmv, then the signal content is recognized as being a part of the tone burst and is amplified. In contrast, if a mixed signal content does not exceed −10 dBmv the content is recognized as noise and the content is not amplified.

In the above example case, the amplification threshold is fixed at a value of −10 dBmv. Fixed amplification thresholds such as this are commonly used with low level expansion techniques used to reduce the internal noise of a typical hearing aid. However, these commonly used low level expansion techniques having a fixed amplification threshold are not effective in reducing noise common to stutter reducing devices because if the threshold is too low, internal noise cannot be suppressed completely. Then again, if the fixed threshold is too high, desirable weak signals such as a whisper will not be amplified.

Figure 7:
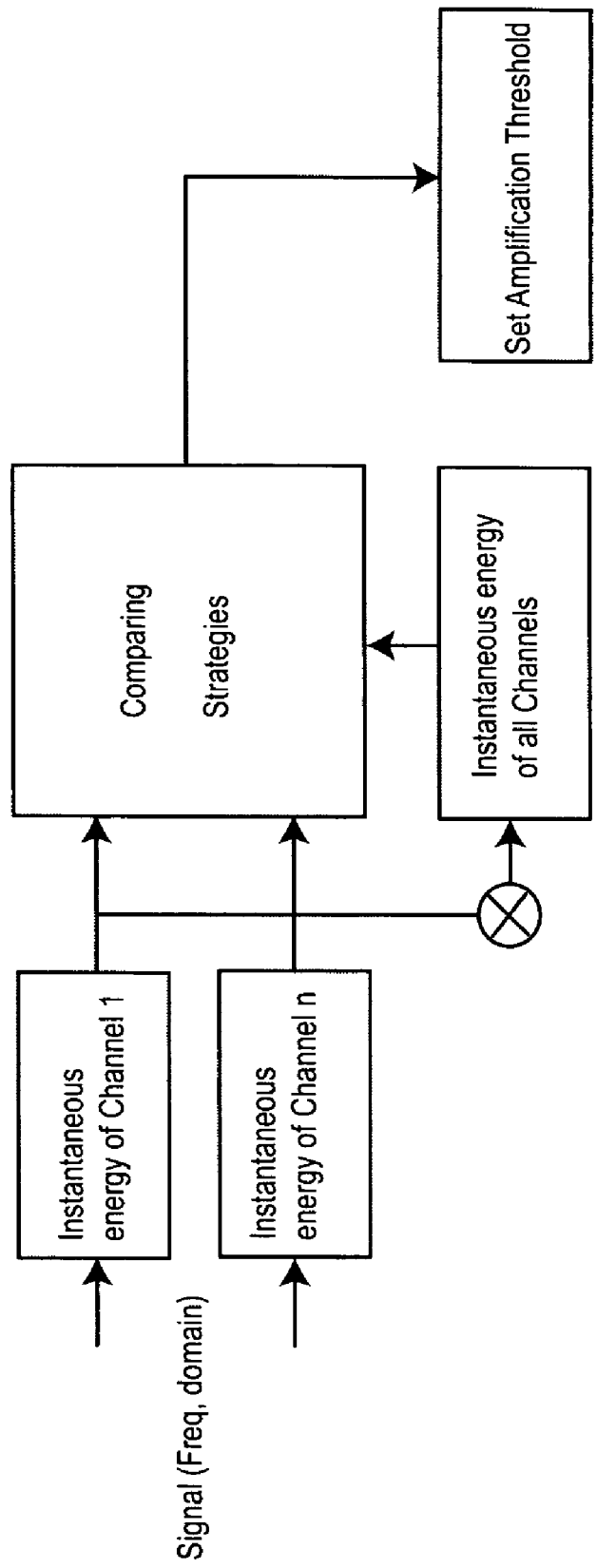
FIG. 7 is a block diagram of the preferred process for dynamically setting the threshold for signal amplification.

The novel low level expansion technique of the present invention solves this problem using a dynamic amplification threshold rather than a fixed amplification threshold. FIG. 7 is a block diagram of the preferred process for dynamically setting the threshold for signal amplification. The low level expansion technique of the present invention analyzes the input signal first, and then dynamically sets the amplification threshold to a higher level to suppress internal noise when there are no speech signals present or in contrast, dynamically sets the amplification threshold to a lower level when there are speech signals to amplify. In particular, the instantaneous energy of channels one through n are each compared against the instantaneous energy of all channels. Comparing Strategies are then used to set a dynamic amplification threshold. As a result of this novel processing technique, any speech signals received by the device will mask weak internal noise so that the noise is significantly tolerable for the user.

Figure 8:
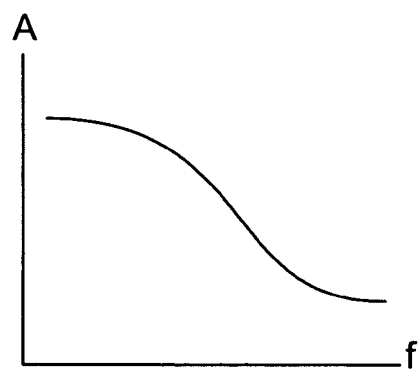
FIG. 8 is a graph showing a typical speech signal without any frequency alteration.
Figure 9:
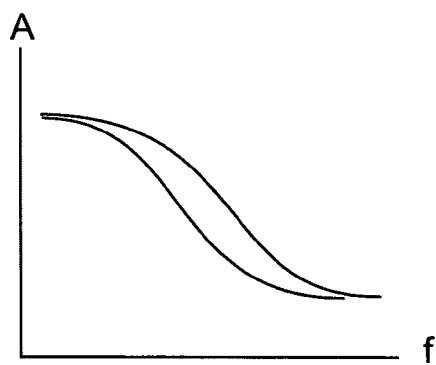
FIG. 9 is a graph showing a typical prior art frequency altered speech spectrum.
Figure 10:
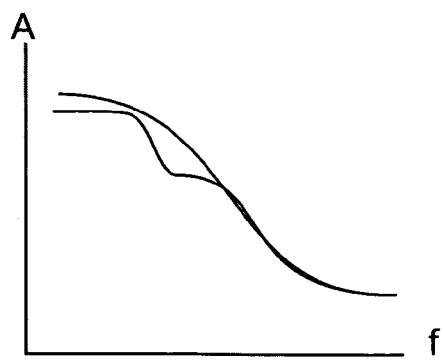
FIG. 10 is a graph showing a band altered frequency speech spectrum according to the present invention.

The invention also provides a method for significantly reducing the undesirable speech distortion present in prior art frequency altered feedback (FAF) based stutter reducing devices. The method provided by the present invention separates any received audio signals into a number of narrow bands. In the preferred embodiment each of the narrow bands have a bandwidth of 500 Hz or smaller. FIGS. 8, 9 and 10 represent the spectrum of a speech signal having amplitudes (A) versus increasing frequency (f). FIG. 8 shows the spectrum of a speech signal without any frequency alteration. FIG. 9 shows a typical prior art frequency altered speech spectrum (bottom curve) compared to the unaltered speech spectrum of FIG. 8. FIG. 10 shows the band altered speech spectrum (bottom curve) provided by the present invention compared to the unaltered speech spectrum of FIG. 8.

Figure 11:
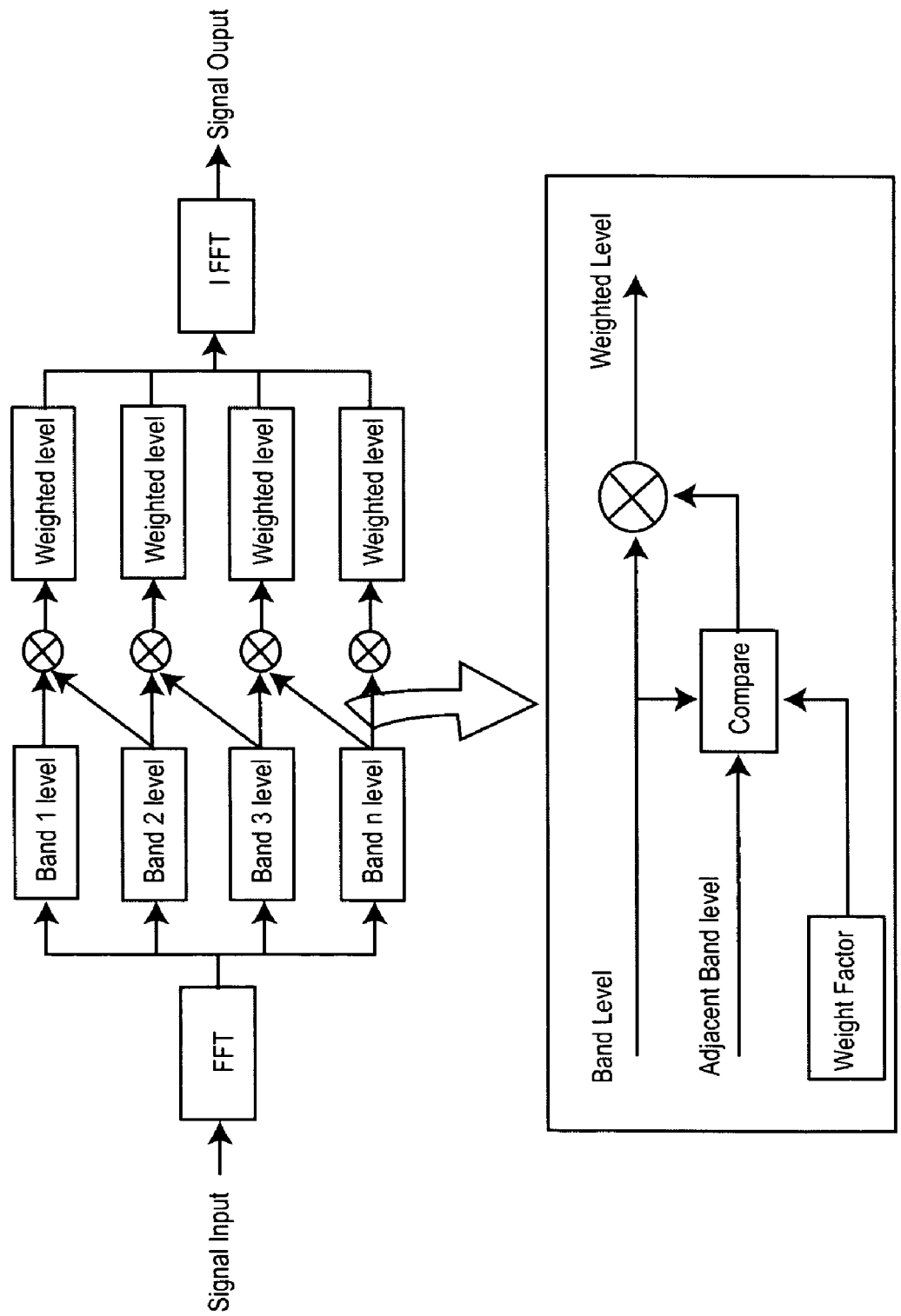
FIG. 11 is a block diagram depicting the signal flow for the band frequency altered feedback of the present invention.

FIG. 11 depicts the signal flow for the band frequency altered feedback of the present invention. Any speech signals processed by the fast Fourier transform (FFT) block are separated into narrow bands 1 through n. Adjacent bands are then mixed and frequency shifted by a weighted level. Bands having a weighted level corresponding to zero shift remain at their natural frequency, while those having weighted level corresponding to a positive or negative shift are respectively shifted up or down in frequency.

Figure 12:
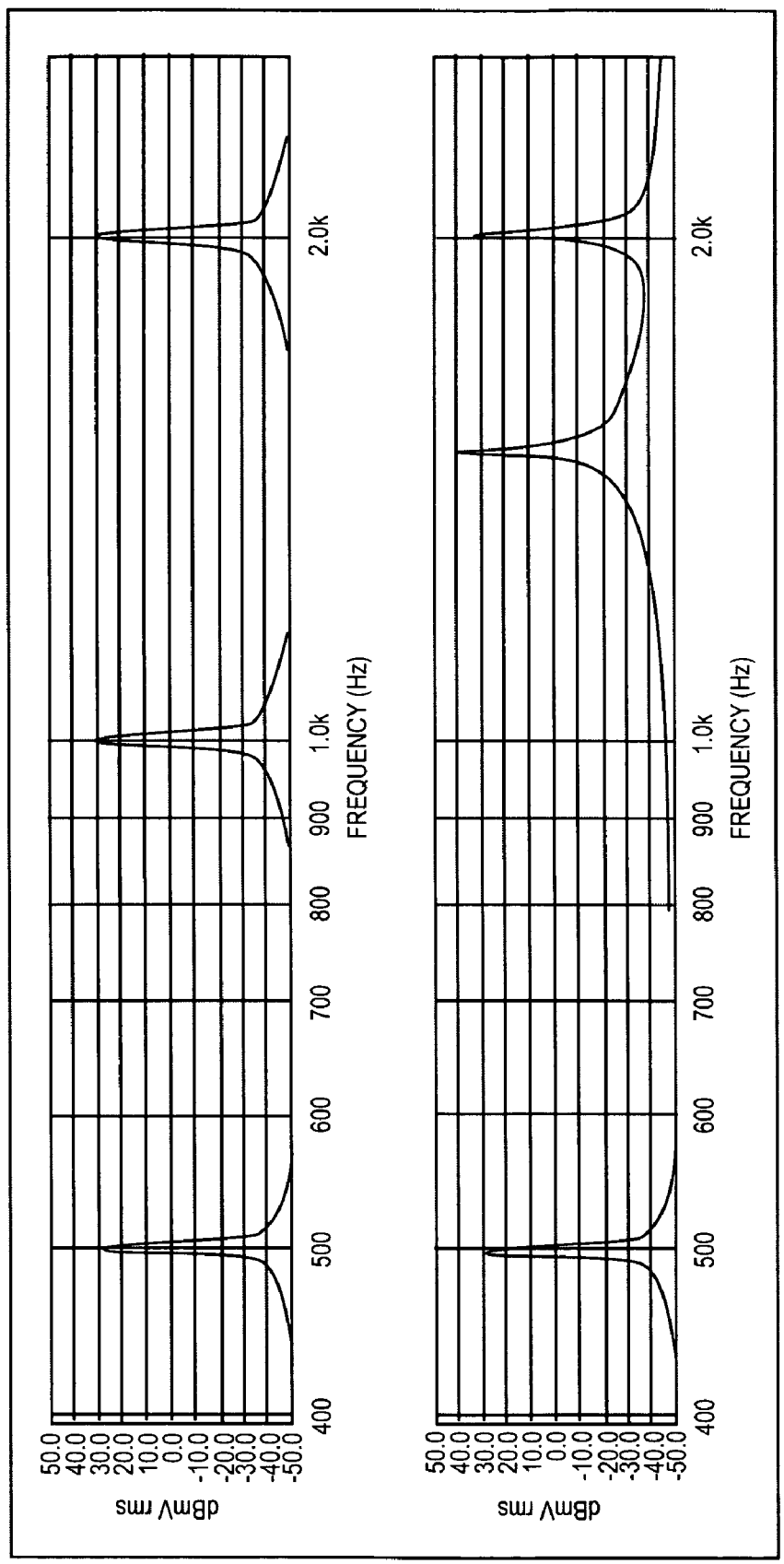
FIG. 12 is a graph comparing the before and after results of band based altered feedback of the present invention.

FIG. 12 depicts the before and after results of band based frequency altered feedback according to the present invention. The upper graph of FIG. 12 depicts a test signal spectrum having a narrow band centered at 1000 Hz before b-FAF. The lower graph of FIG. 12 depicts the results of b-FAF after the 1000 Hz narrow band has been shifted upward by several hundred Hz.

Certain modifications and improvements will occur to those skilled in the art upon a reading of the foregoing description. For example, prior art feedback techniques such as delayed auditory feedback (DAF) and masked auditory feedback (MAF) could be combined with the band-frequency altered feedback (b-FAF) of the present invention to further reduce stuttering in patients that need these additional measures. It should be understood that all such modifications and improvements have been deleted herein for the sake of conciseness and readability, but are properly within the scope of the following claims.

What is claimed is:

1. A wearable stutter reducing device, comprising:
   a) an audio signal receiver for receiving speech signals corresponding to a wearer's voice;
   b) an input conversion means in communication with said audio signal receiver for converting said speech signals and noise mixed with said speech signals into frequency domain components;
   c) a channelization means in communication with said conversion means for separating said frequency domain components into a plurality of channels;
   d) a frequency shifting means to change the frequency of a second predetermined number of said first predetermined number of channels up or down, wherein said second predetermined number is less than said first predetermined number of channels;
   e) an identifying means in communication with said plurality of channels for identifying which channels of said plurality of channels contain substantially more speech corresponding frequency domain components than noise corresponding frequency components;
   f) an amplification means in communication with said identifying means, wherein said amplification means is adjustable to relatively amplify channels identified containing substantially more speech corresponding components than noise corresponding components; and
   g) an output conversion means in communication with said amplification means for converting said frequency components into time domain signals containing amplified speech.

2. The wearable stutter reducing device of claim 1, wherein said audio signal receiver comprises:
   a) an audio transducer having an input and an output; and
   b) an analog-to-digital converter having an input and an output, wherein said analog-to-digital converter input is in communication with said audio transducer output.

3. The wearable stutter reducing device of claim 1, wherein said input conversion means is comprised of a fast Fourier transform.

4. The wearable stutter reducing device of claim 1, wherein said channelization means is comprised of a plurality of digital filters.

5. The wearable stutter reducing device of claim 1, wherein said identifying means uses a signal characteristic to identify signals from noise, said signal characteristic being selected from the group consisting of intensity, intensity change ratio, duration and combinations thereof.

6. The wearable stutter reducing device of claim 1, wherein said amplification means is comprised of a digital signal processor programmable to increase the amplitudes of frequency domain components within channels identified containing substantially more speech corresponding components than noise corresponding components.

7. The wearable stutter reducing device of claim 1, wherein said output conversion means is comprised of an inverse fast Fourier transform.

8. A method for reducing stuttering by providing audible feedback to a person using a wearable stutter reducing device said method comprising:
   a) receiving an audio signal corresponding to the person's speech;
   b) converting said audio signal into frequency domain components;
   c) channelizing said frequency domain components into a first predetermined number of channels;
   d) changing the frequency of a second predetermined number of said first predetermined number of channels up or down, wherein said second predetermined number of channels is less than said first predetermined number of channels;
   e) converting said channelized frequency domain components of said first predetermined number of channels into an audible time domain signal.

9. The method of claim 8, wherein said audio signal is converted into frequency components using a fast Fourier transform.

10. The method of claim 8, wherein said channelizing is accomplished with a plurality of digital filters.

11. The method of claim 8, wherein said converting of said channelized frequency domain components into an audible time domain signal is accomplished using an inverse fast Fourier transform.

12. The method of claim 8, wherein each of said first predetermined number of channels has a bandwidth no greater than 500 Hz.

13. The method of claim 8, wherein said second predetermined number of narrow frequency bands is one and said first predetermined number of channels is more than one.

14. The method of claim 8, wherein said second predetermined number of channels comprises adjacent channels.

15. The method of claim 8, wherein the ratio of the first predetermined number of channels to said second predetermined number of channels is greater than one-to-one.

16. A method for reducing stuttering by providing audible feedback to a person using a wearable stutter reducing device, said method comprising:
   a) receiving audio signals corresponding to the person's speech mixed with noise;
   b) converting said audio signals into frequency domain components;
   c) channelizing said frequency domain components into a first predetermined number of channels;
   d) changing the frequency of a second predetermined number of said first predetermined number of channels up or down, wherein said second predetermined number is less than said first predetermined number of channels;
   e) identifying which of said first predetermined number of channels contain substantially more speech corresponding frequency domain components than noise corresponding frequency domain components;
   f) increasing the amplitudes of frequency domain components within the channels identified as containing substantially more speech corresponding components than noise corresponding components relative to the amplitudes of frequency domain components within channels containing substantially more noise than speech components; and
   g) converting said channelized frequency domain components into an audible time domain signal.

17. The method of claim 16, wherein each of said first predetermined number of channels has a bandwidth no greater than 500 Hz.

18. The method of claim 16, wherein said second predetermined number of said plurality of channels comprises adjacent channels.

19. The wearable stutter reducing device of claim 1, further including a dynamic amplification threshold adjustment means capable of setting said threshold to a high level to suppress internal noise when no speech signal is being received and to set said threshold to a low level when a speech signal is received.

20. A wearable stutter reducing device, comprising:
a) an audio transducer for converting speech signals into electrical signals corresponding to said speech signals, said audio transducer having an input and an output;
b) an analog-to-digital converter having an input in communication with said audio transducer output and an output;
c) a digital signal processor having an input and an output, said input in communication with said analog-to-digital converter, said digital signal processor being programmed to:
  i) convert said speech signals and noise mixed with speech signals into frequency domain components;
  ii) channelize said frequency domain components into a first predetermined number of channels;
  iii) change the frequency of a second predetermined number of said first predetermined number of channels up or down, wherein said second predetermined number is less than said first predetermined number of channels;
  iv) convert said frequency domain components within said first predetermined channels into time domain components;
d) a digital-to-analog converter having an input and an output, said analog-to-digital input being in communication with said digital signal processor output for converting said time domain components into an analog time domain signal; and
e) a speaker having an input in communication with said digital-to-analog converter for producing sound that is responsive to said analog time domain signal.

21. A wearable stuffer reducing device, comprising:
a) an audio signal receiver for receiving speech signals corresponding to a wearer's voice;
b) an input conversion means in communication with said audio signal receiver for converting said speech signals and noise mixed with said speech signals into frequency domain components;
c) a channelization means in communication with said conversion means for separating said frequency domain components into a first predetermined plurality of channels;
d) a frequency shifting means to change the frequency of a second predetermined number of said first predetermined number of channels up or down, wherein said second predetermined number is less than said first predetermined number of channels;
e) an output conversion means in communication with said frequency shifting means for converting said frequency components into time domain signals containing speech.

22. The wearable stutter reducing device of claim 21, further including a noise reduction means and a speech amplification means.

* * * * *

UNITED STATES PATENT AND TRADEMARK OFFICE
CERTIFICATE OF CORRECTION

PATENT NO.        : 7,292,985 B2  
APPLICATION NO.   : 11/001722  
DATED             : November 6, 2007  
INVENTOR(S)       : Tao Jiang et al.

It is certified that error appears in the above-identified patent and that said Letters Patent is hereby corrected as shown below:

Column 10, line 4, "stuffer" should be replaced with --stutter--.

Signed and Sealed this

Second Day of December, 2008

JON W. DUDAS  
*Director of the United States Patent and Trademark Office*